United States Patent [19]

Nowak, Jr. et al.

[11] 4,315,910

[45] Feb. 16, 1982

[54] AEROSOL HAIR SPRAY COMPOSITIONS

[75] Inventors: Frank A. Nowak, Jr., Somerville; Albert L. Micchelli, Middletown, both of N.J.

[73] Assignee: National Starch and Chemical Corporation, Bridgewater, N.J.

[21] Appl. No.: 939,644

[22] Filed: Sep. 5, 1978

Related U.S. Application Data

[63] Continuation-in-part of Ser. No. 776,786, Mar. 11, 1977, abandoned.

[51] Int. Cl.³ .............................................. A61K 7/11
[52] U.S. Cl. ..................................... 424/47; 424/359; 424/361; 424/362
[58] Field of Search .......................................... 424/47

[56] References Cited

U.S. PATENT DOCUMENTS

| | | | |
|---|---|---|---|
| 2,996,471 | 8/1961 | Reiter et al. | 424/47 |
| 3,405,084 | 10/1968 | Bohac et al. | 424/DIG. 1 X |
| 3,417,180 | 12/1968 | Sirota et al. | 424/47 |
| 3,715,428 | 2/1973 | Quasius et al. | 424/47 |
| 3,850,178 | 11/1974 | Schoenholz | 424/47 X |
| 3,862,310 | 1/1975 | Quasius | 424/47 X |
| 3,972,336 | 8/1976 | Nowak, Jr. et al. | 424/47 X |
| 4,030,517 | 6/1977 | Papantoniou et al. | 424/47 X |

Primary Examiner—Dale R. Ore
Attorney, Agent, or Firm—E. Szala; Ellen T. . Dec

[57] ABSTRACT

Aerosol hair spray compositions employing carbon dioxide or hydrocarbon propellants are improved with respect to shelf stability and solubility of the resin by the addition of water.

7 Claims, No Drawings

AEROSOL HAIR SPRAY COMPOSITIONS

CROSS-REFERENCE TO RELATED APPLICATIONS

This application is a continuation-in-part of our co-pending U.S. patent application, Ser. No. 776,786 filed Mar. 11, 1977, now abandoned.

Ecological considerations have recently resulted in a search for suitable substitutes for conventionally employed halocarbons as propellents for aerosol hair spray formulations. Certain hydrocarbons as well as carbon dioxide have been proposed as the most practical and economical replacements. However, the use of these propellents poses a number of problems, some of which are related to the decreased solubility of hair spray resins in the alcohol carbon dioxide or hydrocarbon-propellent systems. Thus, although the commercially favored vinyl acetate/vinyl pyrrolidone copolymers as well as the carboxylated acrylic, maleate and/or acetate based resins are soluble in the anhydrous alcohol-halocarbon systems, the reduced solubility of some of these resins in the proposed anhydrous alcohol-hydrocarbon or carbon dioxide propellent may render the use of these resins unacceptable to the industry. While the use of methylene chloride in amounts of up to about 25% by weight, generally 15-20%, has been proposed in order to increase the solubility of the hair spray resins, the use thereof has been questioned from an economic as well as a safety viewpoint.

The issues of shelf life and metal container corrosion are also critical with regard to hair spray resin formulations. Substantially all hair spray resin formulations available heretofore have been anhydrous due to the belief that in water-containing systems the polymer was rendered unstable and corrosion of the metal container would occur resulting in unacceptable shelf life. Industry has been forced to use formulations employing anhydrous alcohol since the use of water-alcohol mixtures, for example, 95% alcohol, has been found to cause an unacceptable rate of corrosion in uncoated metal containers.

We have now found that the addition of small amounts of water to the hair spray resin not only improves the solubility of the resin in the carbon dioxide or hydrocarbon-alcohol aerosol formulations, but will unexpectedly result in an aerosol formulation with improved stability and reduced can corrosion when compared to similar aerosol formulations to which the water has not been added. Thus, we have found that the addition of water improves the color stability of the polymer solution in the aerosol container. Moreover, accelerated aging tests show that aerosol can corrosion diminishes as the water content is increased within the limits given below.

One of the few areas where water has been employed with hair spray resins has been in the "pump-type" non-pressurized aqueous alcoholic hair setting formulations wherein metal containers are not generally used and wherein relatively long drying periods are involved. Additionally, U.S. Pat. No. 2,995,278 teaches the use of aqueous alcoholic solutions together with halogenated hydrocarbon/hydrocarbon propellent systems, which formulations remain in two separate phases until mixed and propelled using the specialized mixing chamber and valving device.

The present invention is therefore directed to novel aerosol hair spray compositions in aerosol metal containers, said compositions comprising 0.5 to 5.0% by weight of at least one carboxylated or nonionic hair spray resin, 1 to 15% water, a propellent selected from the group consisting of 2-7% carbon dioxide, 5-35% hydrocarbon and mixtures thereof, the remainder of said composition (to 100%) comprising ethanol or isopropanol, or mixtures thereof, with the hair spray resin being soluble in the aerosol composition.

The present invention is therefore equally applicable to use with any of the conventionally employed hair spray resins. Such resins may be generally classified as nonionic and carboxylated resins. The nonionic resins (designated group A) include the resin formed from polyvinyl acetates and copolymers thereof hydrolyzed to an extent that from 15 to 60% of its acetate groups are converted into hydroxyl groups, such as are disclosed in U.S. Pat. No. 3,417,180, the disclosure of which is incorporated herein by reference.

Nonionic resins also include the copolymers of vinyl acetate and vinyl pyrrolidone. While these copolymers may contain vinyl acetate in amounts of 20% or more, it is those copolymers containing at least about 50% vinyl acetate which benefit most from the present invention since the solubility of systems containing less that about 50% vinyl acetate is satisfactory for most formulations. Representative of the nonionic hair spray resins are those available, for example, from BASF under the tradenames Luviskol VA 28 (20% vinyl pyrrolidone, 80% vinyl acetate) and Luviskol VA 37 (30% vinyl pyrrolidone, 70% vinyl acetate). The carboxylated resins useful in the present invention and designated Group B are the carboxylated hair spray resins which comprise organic vinyl polymers containing (i) 5-55 mole per cent acidic monomer such as a monomer selected from the group consisting of maleic acid, maleic anhydride, acrylic acid, methacrylic acid, fumaric acid, itaconic acid, maleic half esters, fumaric half esters, crotonic acid, aconitic acid, allyl acetic acid, allyl arsonic acid, 2-allyl oxypropionic acid, β-benzoyl acrylic acid, N-n-butyl maleamic acid, N-ethyl maleamic acid, N-methyl maleamic acid, N,N-carboxyl-substituted maleamides, 2-furfuryl acrylic acid, 2-vinyl propionic acid, vinyl acetic acid, sorbic acid, dihydroxy maleic acid and mixtures thereof; and (ii) 95-45 mole percent of at least one monomer selected from the group consisting of:

(a) styrene and derivatives thereof, (b) methacrylate and acrylate alkyl esters wherein the alkyl group contains 1 to 18 carbon atoms, (c) vinyl esters of the formula $CH_2=CH-OCOR$ where R is $C_1-C_{18}$, (d) alkyl substituted acrylamides and methacrylamides of the formula $CH_2=CR-CONR_1R_2$ where R is H or $CH_3$; $R_1$ is H or $C_1-C_{12}$ and $R_2$ is $C_1-C_{18}$, (e) diesters of fumaric, itaconic and maleic acids, and, (f) vinyl ethers such as methyl vinyl ether, isobutyl vinyl ether, etc.

In addition to the two monomeric components described above, the carboxylated resin polymer (B) may also contain up to about 30 mole per cent of at least one of the following functional monomers:

(a) hydroxy functional acrylates and methacrylates such as hydroxy ethyl acrylate, hydroxy propyl acrylate, hydroxy ethyl methacrylate, etc.

(b) cationic monomers such as t-butyl aminoethyl methacrylate, dimethyl aminoethyl methacrylate, diethyl aminoethyl methacrylate and the quaternized derivatives thereof such as the quaternized product of 1-chloromethacrylate and trimethylamine or of dimethylaminoethyl methacrylate and dimethyl sulfate;

(c) acrylamide and non-alkyl substituted acrylamides such as diacetone acrylamide;

(d) cyclic amides, such as vinyl pyrrolidone.

Exemplary of such carboxylated hair spray resins are the copolymers of vinyl methyl ether and mono-alkyl esters of maleic anhydride sold by GAF under the GANTREZ trademark; vinyl acetate-crotonic acid copolymers and carboxylated terpolymers of vinyl acetate, crotonic acid and a vinyl ester of an alpha-branched saturated aliphatic monocarboxylic acid containing from 5 to 10 carbon atoms in the carboxylic acid moiety (the latter two resins are respectively described in U.S. Pat. Nos. 2,996,471 and 3,810,977, the disclosures of which are incorporated herein by reference and are available from National Starch and Chemical Corporation under the RESYN trademark); styrene maleic anhydride copolymers and esters thereof (e.g. ARCO's SMA); terpolymers of alkyl acrylamide, acrylamide or methacrylamide, N-vinyl pyrrolidone and acrylic or methacrylic acid sold by American Cyanamid as QUADRAMER; copolymers of N-tert-octylacrylamide, methyl methacrylate, hydroxypropyl methacrylate, acrylic acid and t-butyl aminoethyl methacrylate sold by National Starch and Chemical Corporation under the AMPHOMER trademark, partially hydrolyzed copolymers of acrylic ester with other vinyl monomers (e.g. CIBA 325); terpolymers of vinyl type monomers containing carboxylic groups (e.g. VEM 640-B from the Barr Co.); the interpolymers of various alkyl methacrylates and acrylic acid (e.g. Resin E-1139 available from Rohm and Haas); etc.

All of the previously mentioned carboxylated resins must be reacted with an alkaline reagent to neutralize a portion of the available carboxyl functionalities. In general, neutralization should be carried out to an extent such that at least 3.0% of the carboxyl groups have been reacted. As is recognized by those skilled in the art, the preferred degree of neutralization will vary depending upon the specific carboxylated polymer employed. Thus, the copolymer of octylacrylamide, acrylate and butylaminoethyl methacrylate is generally neutralized to an extent of 70–90% while the copolymers of vinyl methyl ether and the monoalkyl esters of maleic acid are usually neutralized to only about 5–7%. The neutralization may be accomplished using suitable alkaline reagents including sodium and potassium hydroxide, ammonia, primary, secondary and tertiary amines; alkanolamides and hydroxyamines such as 2-amino-2-methyl-1-propanol (AMP) and 2-amino-2-methyl-1,3-propanediol (AMPD).

The neutralization is accomplished by mixing the resin in the form of a solution in an organic solvent, with or without added water, with a concentration of the alkaline reagent approximately equimolar to the percent of the carboxyl groups to be neutralized. The choice of the alkaline reagent as well as the degree of neutralization affects not only the water solubility or dispersibility of the resultant resin thus permitting easy removal of the resin from the hair by merely washing with shampoo but also affects the flexibility of the resultant film when sprayed on the hair. Thus, a particular reagent may be selected or the degree of neutralization can be regulated to produce a soft film, normal film or a film suitable for "hard-to-hold" hair. A further description of the neutralization is presented, for example, in U.S. Pat. No. 2,996,471, the disclosure of which is incorporated herein by reference.

The selected resin, dissolved in an appropriate solvent, is then admixed with water prior to being charged into the aerosol container. Suitable solvents include ethanol, isopropanol and mixtures thereof. The amount of water employed should be less than about 15% by weight of the total formulation and at least about 1%. It will be apparent that the higher levels of water will result in a hair spray film which will take longerr to dry when applied to the hair. Formulations using water in amounts of 3 to 8% by weight of the total formulation are preferred. It is noted that according to prior art formulations, it was required that alcohols used as solvents be employed as anhydrous alcohols and it is therefore an added feature of the present invention, that alcohol-water mixtures may be employed in the present formulations thus presenting substantial economic savings. If aqueous alcohol mixtures are employed, the amount of water in the non-anhydrous alcohol is included when calculating the total water present in the aerosol formulation.

The propellent employed in the present formulation is either carbon dioxide or a suitable hydrocarbon propellent or mixtures thereof. Suitable hydrocarbon propellents include, for example, propane, isobutane, n-butane, 2,2-dimethyl propane and isopentane. If only carbon dioxide is employed, amounts of 2 to 7% are satisfactory. In the case of hydrocarbon propellents, amounts of 5 to 35% may be employed. It will be understood that when mixtures of carbon dioxide and hydrocarbon are used as propellents, the amount required will vary based on the relative proportions of the propellent components. Among the most commonly employed propellent mixtures are those which use propane and/or isobutane together with the carbon dioxide. Typical of such propellent mixtures is a blend of approximately 1 part carbon dioxide and 6 parts A46 (a blend of isobutane and propane).

Optional additives may be incorporated into the aerosol formulations of this invention in order to modify certain properties thereof. Among these additives may be included: plasticizers such as glycols, phthalate esters and glycerine; silicones; emollients, lubricants and penetrants such as lanolin compounds; protein hydrolyzates and other protein derivatives, ethylene oxide adducts and polyoxyethylene cholesterol; dyes, tints, and other colorants; and perfumes.

In general, the formulations of the present invention can be prepared by merely dissolving the resin in the solvent, adding the neutralizing agent if required, and the desired amount of water, as well as any modifying agents, and then charging this "concentrate" into the aerosol container. The aerosol valve is then crimped in place and the propellent added. Carbon dioxide is added either as a gas or in the form of an alcoholic solution using conventional techniques. Hydrocarbons are added in liquid from under pressure.

With regard to proportions, the final aerosol formulations typically contain the hair spray resin which, in the case of the carboxylated resins, has been neutralized to the degree desired, in a concentration of form 0.5 by weight of 5.0%, preferably 0.5 to 2.5%; water in an amount of 1 to 15%, preferably 3 to 8%, carbon dioxide propellent in an amount of 2 to 7%, preferably 4 to 6% or hydrocarbon propellent in an amount of 5 to 35%, preferably 15 to 20%, with the remainder of the composition (to a total of 100%) being ethanol or isopropanol or mixtures thereof. It should be recognized that the latter proportions should be considered as being merely illustrative inasmuch as it may well be possible to prepare operable formulations having concentrations of components which fall outside the above suggested ranges.

The resulting hair fixing formulations exhibit all of the characteristics required of such a product, resulting in films which hold the hair well and which are easily removed by shampooing.

In the following examples, which further illustrate this invention, all parts given are by weight unless otherwise indicated.

EXAMPLE I

This example illustrates the preparation of an aerosol hair spray formulation representative of the present invention.

Two parts of a carboxylated acrylic copolymer (available from Rohm and Haas as Resin E-1139) was neutralized with 0.18 parts of 2-amino-2-methyl-1-propanol (AMP). The neutralized resin was then dissolved in 87.82 parts anhydrous ethanol and 5 parts water were added thereto. The thus prepared concentrate was then added to an aerosol can (half pound tinplate with tin side seam) which was purged to eliminate air. The aerosol valve was then emplaced and crimped onto the can and carbon dioxide was added through the valve until 5 parts by weight had been picked up.

The resulting aerosol formulation was stable over an extended period of time and when sprayed resulted in a satisfactory hair holding film which could be readily removed by shampooing.

EXAMPLE II

This example demonstrates the beneficial effects contributed by the presence of water in the hair spray formulations of the present invention.

Two series of samples, each series comprising 10 (6 oz.) cans (half pound tinplate with tin side seam) were prepared. One series was charged with the formulation of EX. I (designated series A) and the other series (designated series B) charged with a similar formulation containing 92.82 parts anhydrous ethanol and no water. The cans were incubated at 120° F. At six week intervals (each equivalent to approximately 1 year at room temperature), for a period of 18 weeks, two cans of each formulation were removed from the oven, cooled to room temperature and then opened and the concentrate evaluated for color and pH. The amount of can corrosion was also observed.

The results are as follows:

1. After the first six weeks, detinning (a sign of corrosion of the tin lining as evidenced by the formation of black spots and blotches) was evident throughout the interiors of the can filled with formulations of Series B which contained no water. The condition became worse with time and at 18 weeks was of significant proportion.

2. During the 18 week period insignificant detinning was noted (in some cases none at all) on the cans of Series A containing formulations of the present invention.

3. No difference in concentrate color or pH was observed between the two samples.

4. All cans were relatively stable in pressure.

EXAMPLE III

The following experiment was performed in order to show the improvement in solubility with increased water content in accordance with the present invention.

Three formulations were prepared using the general procedure of Example I. The formulations were filled in glass vessels fitted with a thermocouple device. The filled vessels were chilled slowly until turbidity signifying resin insolubility developed. The resultant "cloud point", i.e. the temperature at which the polymer can be seen to precipitate from the solution, was recorded. A lower cloud point indicates better solubility.

The specific formulations and corresponding cloud points are shown in Table I.

TABLE I

| Formulations | A | B | C |
| --- | --- | --- | --- |
| Resin E-1139 | 2.00 | 2.00 | 2.00 |
| AMP | 0.18 | 0.18 | 0.18 |
| Anhydrous Ethanol | 92.82 | 87.82 | 82.82 |
| Distilled water | — | 5.00 | 10.00 |
| Carbon Dioxide | 5.00 | 5.00 | 5.00 |
| Cloud Point °F. | +48° | −22° | below −58° |

As is shown by the observed results, the addition of water to the hair spray formulation provides an impressive improvement in the solubility of the carboxylated vinyl polymer contained therein.

EXAMPLE IV

This example illustrates the use of vinyl acetatecrotonic acid type polymers in the aerosol composition of the present invention.

Two carboxylated polymers available from National Starch and Chemical Corporation under the tradenames RESYN 28-1310 and RESYN 28-2930 comprising respectively a copolymer of vinyl acetate and crotonic acid and a terpolymer of vinyl acetate, crotonic acid and vinyl neodecanoate were employed to produce aerosol formulations using the procedure outlined in Example I. The specific formulations using the procedure outlined in Example I are shown in Table II below:

TABLE II

| Formulations | A | B | C | D | E | F |
| --- | --- | --- | --- | --- | --- | --- |
| RESYN 28-2930 | 1.50 | 1.50 | 1.50 | — | — | — |
| RESYN 28-1310 | — | — | — | 1.50 | 1.50 | 1.50 |
| AMP | 0.12 | 0.12 | 0.12 | 0.12 | 0.12 | 0.12 |
| Anhydrous Ethanol | 93.38 | 90.88 | 88.38 | 93.38 | 90.88 | 88.38 |
| Distilled water | — | 2.50 | 5.00 | — | 2.50 | 5.00 |
| Carbon dioxide | 5.00 | 5.00 | 5.00 | 5.00 | 5.00 | 5.00 |

The aerosol formulations were stored and evaluated at 2, 4, 6, 12 and 24 week intervals following the procedure used in Example I. The observed results follow:

Formulations A–C

1. Less discoloration of the concentrate was observed in the samples containing larger amounts of water for all the time periods.

2. Less detinning was observed in formulations containing water at 6, 12 and 24 week intervals. No differences in can corrosion were observed at the 2 and 4 week intervals.

Formulations D-F

1. Less concentrate discoloration was observed at all time intervals in the samples containing larger amounts of water.
2. Less detinning was observed in formulations containing water at all time intervals.
3. The resin precipitated at the 24 week interval in the formulations containing no water. The samples containing water remained homogeneous.

EXAMPLE V

This example illustrates the increased solubility obtained by the addition of water to hair spray formulations containing carboxylated resins and the effect of increased neutralization and solid content of the polymer on the level of solubility. A series of aerosol formulations were prepared using the vinyl acetate crotonic acid polymers of Example IV. The formulations were tested for solubility using the cloud point testing procedure described in Example III. Formulations and results are shown in Table III.

TABLE III

| Formulations AA | | | | | | |
|---|---|---|---|---|---|---|
| RESYN 28-1310 | 1.50 | 1.50 | 1.50 | 1.50 | 1.50 | 1.50 |
| AMP | 0.12 | 0.12 | 0.12 | 0.12 | 0.12 | 0.12 |
| Anhydrous ethanol | 93.38 | 92.38 | 90.88 | 88.38 | 83.38 | 73.38 |
| Distilled water | 0.0 | 1.00 | 2.50 | 5.00 | 10.00 | 20.00 |
| Carbon dioxide | 5.00 | 5.00 | 5.00 | 5.00 | 5.00 | 5.00 |
| Cloud Point (°F.) | 75° | 66° | 57° | 37° | −11° | −33° |
| Formulations BB | | | | | | |
| RESYN 28-1310 | 2.00 | 2.00 | 2.00 | 4.00 | 4.00 | 4.00 |
| AMP | 0.16 | 0.16 | 0.16 | 0.32 | 0.32 | 0.32 |
| Anhydrous ethanol | 92.84 | 87.84 | 82.84 | 90.68 | 85.68 | 80.68 |
| Distilled water | 0.0 | 5.00 | 10.00 | 0.0 | 5.00 | 10.00 |
| Carbon dioxide | 5.00 | 5.00 | 5.00 | 5.00 | 5.00 | 5.00 |
| Cloud Point (°F.) | +61° | −1° | −20° | +56° | −10° | −20° |
| Formulations CC | | | | | | |
| RESYN 28-2930 | 2.00 | 2.00 | 2.00 | 2.00 | 2.00 | |
| AMP | 0.17 | 0.17 | 0.17 | 0.17 | 0.17 | |
| Anhydrous ethanol | 92.83 | 92.33 | 89.83 | 86.78 | 80.73 | |
| Distilled water | 0.0 | 0.50 | 3.00 | 6.05 | 12.10 | |
| Carbon dioxide | 5.00 | 5.00 | 5.00 | 5.00 | 5.00 | |
| Cloud Point (°F.) | +33° | +23° | 31.5° | −10° | −26° | |
| Formulations DD | | | | | | |
| RESYN | 2.00 | 2.00 | 2.00 | 2.00 | 4.00 | 4.00 |
| AMP | 0.20 | 0.20 | 0.20 | 0.20 | 0.33 | 0.33 |
| Anhydrous ethanol | 92.80 | 92.30 | 89.80 | 86.80 | 90.67 | 80.67 |
| Distilled water | 0.0 | 0.50 | 3.00 | 6.00 | 10.00 | |
| Carbon dioxide | 5.00 | 5.00 | 5.00 | 5.00 | 5.00 | 5.00 |
| Cloud Point (°F.) | +28° | +16° | −10° | −25° | +4° | −20° |

The cloud points shown above indicate the improved solubility characteristic of the compositions of the present invention.

EXAMPLE VI

In another aspect of this example the Resyn 28-2930 polymer was used in a hair spray formulation wherein a hydrocarbon mixture was used as propellent. The procedure and Cloud Point test discussed in the previous examples were repeated using the following formulation:

| | | | |
|---|---|---|---|
| RESYN 28-2930 | 2.00 | 2.00 | 2.00 |
| AMP | 0.17 | 0.17 | 0.17 |
| Anhydrous ethanol | 77.83 | 74.83 | 71.83 |
| H₂O | — | 3.00 | 6.00 |
| Isobutane | 18.00 | 18.00 | 18.00 |
| Propane | 2.00 | 2.00 | 2.00 |
| Cloud Point (°F.) | 16° | <−30° | <−30° |

EXAMPLE VII

As already discussed, carbon dioxide-propelled aerosol formulations can be prepared using the basic procedure described in Example I with any carboxylated resins comprising the following monomeric components:

TABLE IV

| Formulations | A | B | C | D | E | F | G | H |
|---|---|---|---|---|---|---|---|---|
| Vinyl Acetate | 90 | | 80 | 70 | 70 | 70 | | |
| t-Octyl Methacrylamide | | 50 | | | | | | 50 |
| Methyl Methacrylate | | 20 | | | | | | |
| Methyl Acrylate | | 10 | | | | | | 10 |
| Isobutyl Vinyl Ether | | | | 15 | | | | |
| Styrene | | | | | | | 60 | 15 |
| Crotonic Acid | | | 10 | | | | | |
| Acrylic Acid | | 10 | | | 10 | | | |
| Mono-ethyl Maleate | 10 | | | 10 | 15 | | 30 | |
| Maleic Acid | | | | | | | | 15 |
| Hydroxy Propyl Acrylate | | | 5 | | | | | 10 |
| Diacetone Acrylamide | | | 5 | | 5 | 10 | | |
| Vinyl Pyrrolidone | | | | | 15 | | | |
| Di-Octyl Maleate | | | | | | | 10 | 10 |
| Acrylamide | | 10 | | | | | | |

In all cases, aerosol formulations containing the above carboxylated polymers, when neutralized to the desired extent, will exhibit improved solubility and shelf life in carbon dioxide/alcohol systems when water is added according to the teachings of the present invention.

EXAMPLE VIII

This example illustrates the use of 95% ethanol in the formulation of the present invention.

Two parts of a carboxylated polyvinyl acetate copolymer used in Sample D, E and F of Example IV were mixed with 0.16 parts of 2-amino-2-methyl-1-propanol and 92.84 parts of 95% ethanol. Mixing was continued until solution was complete. The thus prepared concentrate was then added to an aerosol can which was purged to eliminate air. The aerosol valve was then emplaced and crimped onto the can and carbon dioxide was added through the valve until 5 parts by weight had been picked up.

It was found that the resulting aerosol hair spray formulation when sprayed resulted in a satisfactory hair holding film which could be readily removed by shampooing. Moreover, the aerosol formulation displayed superior low temperature stability and can stability when compared to a formulation made with anhydrous ethanol and no externally added water.

EXAMPLE IX

This example shows the superior solubility experienced by the formulations of the present invention as compared with those of the prior art wherein methylene chloride is used to improve solubility. The example also shows the use of both hydrocarbon and carbon dioxide propellents in the present formulations.

The preparative and testing procedures described in the previous examples were repeated using the formulations shown below.

| Formulation IX-A | | | | | |
|---|---|---|---|---|---|
| RESYN 28-2930 | 2.00 | 2.00 | 2.00 | 2.00 | 2.00 |
| AMP | 0.17 | 0.17 | 0.17 | 0.17 | 0.17 |
| Anhydrous ethanol | 77.83 | 72.83 | 62.83 | 76.83 | 75.33 |
| Distilled water | — | — | — | 1.00 | 2.50 |
| Methylene Chloride | — | 5.00 | 15.00 | — | — |
| Isobutane | 18.00 | 18.00 | 18.00 | 18.00 | 18.00 |
| Propane | 2.00 | 2.00 | 2.00 | 2.00 | 2.00 |
| Cloud Point (°F.) | 18° | 2° | −27° | −5° | <−30° |
| Formulation IX-B | | | | | |
| RESYN 28-1310 | 2.00 | 2.00 | 2.00 | 2.00 | 2.00 |
| AMP | 0.17 | 0.17 | 0.17 | 0.17 | 0.17 |
| Anhydrous ethanol | 77.83 | 72.83 | 57.83 | 75.33 | 72.83 |
| Distilled water | — | — | — | 2.5 | 5.00 |
| Methylene Chloride | — | 5.00 | 20.00 | — | — |
| Isobutane | 18.00 | 18.00 | 18.00 | 18.00 | 18.00 |
| Propane | 2.00 | 2.00 | 2.00 | 2.00 | 2.00 |
| Cloud Point (°F.) | 65° | 50° | 5° | 25° | −12° |
| Formulation IX-C | | | | | |
| RESYN 28-2930 | 2.00 | 2.00 | 2.00 | 2.00 | 2.00 |
| AMP | 0.17 | 0.17 | 0.17 | 0.17 | 0.17 |
| Anhydrous ethanol | 92.83 | 87.83 | 82.83 | 90.83 | 86.83 |
| Distilled water | — | — | — | 2.00 | 6.00 |
| Methylene Chloride | — | 5.00 | 10.00 | — | — |
| Carbon Dioxide | 5.00 | 5.00 | 5.00 | 5.00 | 5.00 |
| Cloud Point (°F.) | 31° | 13° | −3° | 4° | −20° |
| Formulations IX-D | | | | | |
| RESYN 28-1310 | 2.00 | 2.00 | 2.00 | 2.00 | 2.00 |
| AMP | 0.17 | 0.17 | 0.17 | 0.17 | 0.17 |
| Anhydrous ethabol | 92.83 | 87.83 | 67.83 | 90.83 | 86.83 |
| Distilled water | — | — | — | 2.00 | 6.00 |
| Methylene Chloride | — | 5,00 | 2.00 | — | — |
| Carbon Dioxide | 5,00 | 5.00 | 5.00 | 5.00 | 5.00 |
| Cloud Point (°F.) | 62° | 47° | 7° | 35° | −15° |

As is shown by the above results, the addition of relatively small amounts of water to the aerosol hair spray formulations results in a marked improvement in solubility over that obtained using much larger amounts of methylene chloride.

EXAMPLE X

This example illustrates the use of conventional nonionic hair spray resins in accordance with the present invention. The preparative and testing procedures described in Example I were used to prepare the aerosol formulations shown in the following table.

| RESYN 959C (1) | 3.33 | 3.33 | — | — | — | — |
|---|---|---|---|---|---|---|
| Luviskol VA55 I (2) | — | — | 4.00 | 4.00 | — | — |
| Luviskol VA37 I (3) | — | — | — | — | 4.00 | 4.00 |
| Anhydrous Ethanol | 76.67 | 70.67 | — | — | 76.00 | 70.00 |
| Anhydrous Isopropanol | — | — | 71.00 | 65.00 | — | — |
| Distilled Water | — | 6.00 | — | 6.00 | — | 6.00 |
| Isobutane | 18.00 | 18.00 | 22.50 | 22.50 | 18.00 | 18.00 |
| Propane | 2.00 | 2.00 | 2.50 | 2.50 | 2.00 | 2.00 |
| Cloud Point (°F.) | 70° | 4° | 8° | −30° | 27° | −30° |

(1) 40% Hydrolyzed polyvinyl acetate (avg. molecular wt. 11,000).
(2) Copolymer of 50% vinyl pyrrolidone and 50% vinyl acetate.
(3) Copolymer of 30% vinyl pyrrolidone and 70% vinyl acetate.

Summarizing, it is illustrated by the examples presented herein that the addition of small amounts of water to a carbon dioxide or hydrocarbon-propelled aerosol hair spray formulation unexpectedly greatly increases the solubility of the conventional hair spray resin while increasing the shelf stability of the aerosol mixture in the container.

Variations may be made in proportions, procedures and materials without departing from the scope of the invention as defined by the following claims.

We claim:

1. Aerosol hair spray compositions in aerosol metal containers comprising 0.5 to 5% of at least one hair spray resin selected from the group consisting of:
    (A) a carboxylated organic vinyl polymer containing:
        (i) 5-55 mole percent acidic monomer selected from the group consisting of maleic acid, maleic anhydride, acrylic acid, methacrylic acid, fumaric acid, itaconic acid, maleic half esters, fumaric half esters, crotonic acid, aconitic acid, allyl acetic acid, allyl arsonic acid, 2-allyl oxypropionic acid, β-benzoyl acrylic acid, N-n-butyl maleamic acid, N-ethyl maleamic acid, N-methyl maleamic acid, N,N-carboxyl-substituted maleamides, 2-furfuryl acrylic acid, 2-vinyl propionic acid, vinyl acetic acid, sorbic acid, dihydroxy maleic acid and mixtures thereof;
        (ii) 95-45 mole percent of at least one monomer selected from the group consisting of:
            (a) styrene and derivatives thereof;
            (b) methacrylate and acrylate alkyl esters wherein the alkyl group contains 1 to 18 carbon atoms,
            (c) vinyl esters of the formula $CH_2=CH-O-COR$ wherein R is $C_1-C_{18}$,
            (d) alkyl substituted acrylamides and methacrylamides of the formula $CH_2=CR-CONR_1R_2$ wherein R is H or $CH_3$, $R_1$ is H or $C_1-C_{12}$ and $R_2$ is $C_1-C_{18}$,
            (e) diesters of fumaric, itaconic and maleic acids, and
            (f) vinyl ethers; and
        (iii) 0-30 mole percent of at least one monomer selected from the group consisting of:
            (a) hydroxy functional acrylates and methacrylates,
            (b) cationic monomers selected from the group consisting of t-butyl aminoethyl methacrylate, dimethyl aminoethyl methacrylate, diethyl aminoethyl methacrylate, and the quaternized derivatives thereof,
            (c) acrylamide and non-alkyl substituted acrylamides, and
            (d) cyclic amides, wherein said carboxylated polymer is neutralized to an extent that 3 to 100% of the carboxyl groups have been reacted; and
    (B) a nonionic resin selected from the group consisting of polyvinyl acetate hydrolyzed to an extent that from 15 to 60% of its acetate groups are converted into hydroxyl groups and copolymers of vinyl acetate and vinyl pyrrolidone containing at least about 50% vinyl acetate; 1 to 15% water, a propellent selected from the group consisting of 2-7% carbon dioxide, 5-35% hydrocarbon and mixtures thereof, the remainder of said composition to equal 100%, comprising ethanol or isopropanol or mixtures thereof, all percentages expressed by weight, said hair spray resin being soluble in said composition.

2. An aerosol hair spray composition according to claim 1 wherein the hair spray resin is a copolymer of vinyl acetate and crotonic acid.

3. An aerosol hair spray composition according to claim 1 wherein the hair spray resin is a terpolymer of vinyl acetate, crotonic acid and a vinyl ester of an alpha-branched saturated aliphatic monocarboxylic acid containing from 5 to 10 carbon atoms in the carboxylic acid moiety.

4. An aerosol hair spray composition according to claim 1 wherein the hair spray resin comprises a copolymer of 20-30% vinyl pyrrolidone and 70-80% vinyl acetate.

5. An aerosol hair spray composition according to claim 1 wherein the water is present in an amount of 3 to 8% by weight.

6. An aerosol hair spray composition according to claim 1 wherein the propellant is a mixture comprising 90% isobutane and 10% propane.

7. A process for increasing the solubility of a hair spray resin selected from the group consisting of
(A) a carboxylated organic vinyl polymer containing:
  (i) 5–55 mole percent acidic monomer selected from the group consisting of maleic acid, maleic anhydride, acrylic acid, methacrylic acid, fumaric acid, itaconic acid, maleic half esters, fumaric half esters, crotonic acid, aconitic acid, allyl acetic acid, allyl arsonic acid, 2-allyl oxypropionic acid, β-benzoyl acrylic acid, N-n-butyl maleamic acid, N-ethyl maleamic acid, N-methyl maleamic acid, N,N-carboxyl-substituted maleamides, 2-furfuryl acrylic acid, 2-vinyl propionic acid, vinyl acetic acid, sorbic acid, dihydroxy maleic acid and mixtures thereof;
  (ii) 95–45 mole percent of at least one monomer selected from the group consisting of:
    (a) styrene and derivatives thereof;
    (b) methacrylate and acrylate alkyl esters wherein the alkyl group contains 1 to 18 carbon atoms,
    (c) vinyl esters of the formula $CH_2=CH=O-COR$ wherein R is $C_1-C_{18}$,
    (d) alkyl substituted acrylamides and methacrylamides of the formula $CH_2=CR-CONR_1R_2$ wherein R is H or $CH_3$, $R_1$ is H or $C_1-C_{12}$ and $R_2$ is $C_1-C_{18}$,
    (e) diesters of fumaric, itaconic and maleic acids, and
    (f) vinyl esters; and
  (iii) 0–30 mole percent of at least one monomer selected from the group consisting of:
    (a) hydroxy functional acrylates and methacrylates,
    (b) cationic monomers selected from the group consisting of t-butyl aminoethyl methacrylate, dimethyl aminoethyl methacrylate, diethyl aminoethyl methacrylate, and the quaternized derivatives thereof,
    (c) acrylamide and non-alkyl substituted acrylamides, and
    (d) cyclic amides, wherein said carboxylated polymer is neutralized to an extent that 3 to 100% of the carboxyl groups have been reacted; and
(B) a nonionic resin selected from the group consisting of polyvinyl acetate hydrolyzed to an extent that from 15 to 60% of its acetate groups are converted into hydroxyl groups and copolymers of vinyl acetate and vinyl pyrrolidone containing at least about 50% vinyl acetate, in an aerosol hair spray composition of the type containing 0.5 to 5% of said resin, a propellant selected from the group consisting of 2–7% carbon dioxide, 5–35% hydrocarbon, and mixtures thereof, all percentages expressed by weight, and a solvent comprising ethanol, isopropanol or mixtures thereof, said process comprising adding to said composition 1–15% water, by total weight of the composition, thereby rendering said hair spray resin soluble in said composition.

* * * * *